(12) United States Patent
Bouwman et al.

(10) Patent No.: US 10,590,064 B2
(45) Date of Patent: Mar. 17, 2020

(54) CRYSTALS OF ALANINE N-ACETIC ACID PRECURSORS, PROCESS TO PREPARE THEM AND THEIR USE

(71) Applicant: NOURYON CHEMICALS INTERNATIONAL B.V., Arnhem (NL)

(72) Inventors: Albertus Jacobus Maria Bouwman, Groessen (NL); Hubertus Johannes Jongen, Gendringen (NL); Roy Gérard Doppen, Deventer (NL); Martin Heus, Arnhem (NL); Elwin Schomaker, Arnhem (NL)

(73) Assignee: NOURYON CHEMICALS INTERNATIONAL B.V., Arnhem (NL)

( * ) Notice: Subject to any disclaimer, the term of this patent is extended or adjusted under 35 U.S.C. 154(b) by 0 days.

(21) Appl. No.: 15/538,559

(22) PCT Filed: Dec. 21, 2015

(86) PCT No.: PCT/EP2015/080837
§ 371 (c)(1),
(2) Date: Jun. 21, 2017

(87) PCT Pub. No.: WO2016/102494
PCT Pub. Date: Jun. 30, 2016

(65) Prior Publication Data
US 2017/0334833 A1    Nov. 23, 2017

(30) Foreign Application Priority Data

Dec. 23, 2014 (EP) .................................. 14200045

(51) Int. Cl.
| | | |
|---|---|---|
| *C07C 227/26* | (2006.01) | |
| *C07C 237/06* | (2006.01) | |
| *C07C 255/25* | (2006.01) | |
| *C07C 231/24* | (2006.01) | |
| *C07C 253/30* | (2006.01) | |
| *C07C 253/34* | (2006.01) | |

(52) U.S. Cl.
CPC .......... *C07C 227/26* (2013.01); *C07C 231/24* (2013.01); *C07C 237/06* (2013.01); *C07C 253/30* (2013.01); *C07C 253/34* (2013.01); *C07C 255/25* (2013.01)

(58) Field of Classification Search
None
See application file for complete search history.

(56) References Cited

U.S. PATENT DOCUMENTS

| | | | |
|---|---|---|---|
| 2,511,487 A | 6/1950 | Thompson | |
| 3,679,728 A | 7/1972 | Morgan et al. | |
| 3,679,729 A | 7/1972 | Daniels | |
| 4,478,759 A | 10/1984 | Distler et al. | |
| 4,510,099 A | 4/1985 | Stern | |
| 5,786,313 A | 7/1998 | Schneider et al. | |
| 5,849,950 A | 12/1998 | Greindl et al. | |
| 6,005,141 A | 12/1999 | Schneider et al. | |
| 7,671,234 B2 | 3/2010 | Oftring et al. | |
| 7,754,911 B2 | 7/2010 | Oftring et al. | |
| 8,802,894 B2 | 8/2014 | Oftring et al. | |
| 2012/0184769 A1 | 7/2012 | Judat et al. | |
| 2012/0248370 A1 | 10/2012 | Oftring et al. | |
| 2012/0283473 A1* | 11/2012 | Oftring | ................ C07C 227/42 562/571 |

FOREIGN PATENT DOCUMENTS

| | | |
|---|---|---|
| CN | 102993034 A | 3/2013 |
| CN | 103910651 A | 7/2014 |
| CN | 203763892 U | 8/2014 |
| JP | S55-122751 A | 9/1980 |
| JP | H11-21585 A | 1/1999 |
| JP | H11-502834 A | 3/1999 |
| JP | H11-92436 A | 4/1999 |
| WO | 96/030335 | 3/1996 |
| WO | 96/30335 A1 | 10/1996 |
| WO | 2009/024519 A1 | 2/2009 |
| WO | 2014/012990 A1 | 1/2014 |

(Continued)

OTHER PUBLICATIONS

XP002741568; Nov. 21, 2014; Database CHEMCATS [Online]; Aldlab Chemicals Building Blocks; Database accession No. 1343771791; CAS RN: 1497422-52-2; Order No. AX104674167.
XP002741569; Nov. 21, 2014; Database Registry Chemical Abstracts Service, Columbus, Ohio, US; Database accession No. 1508279-60-4; CAS RN: 1508279-60-4.
International Search Report and Written Opinion for PCT/EP2015/080837 dated Mar. 11, 2016.
European Search Report issued in EP Application No. 14200045. 4-1451 dated Jul. 17, 2015.

(Continued)

*Primary Examiner* — Ana Z Muresan
(74) *Attorney, Agent, or Firm* — Lorenz & Kopf, LLP

(57) ABSTRACT

The present invention relates to alanine N-acetic acid precursors of formula (i) COOM-CH(CH3)—NH—(CH2CN), wherein M is hydrogen (alanine N-monoacetonitrile), or (ii) COOM-CH(CH3)—N—(CH2CN)2, wherein 0 to 50% of all M is sodium or potassium and 50 to 100% of all M is hydrogen (alanine N,N-diacetonitrile and its partial sodium or potassium salts) comprising L-alanine to D-alanine in a range of from 75:25 to 50:50 (L:D), or (iii) COOM-CH (CH3)—N—(CH2CONH2)2, wherein M is hydrogen (alanine N,N-diacetamide), in the form of crystals, and relates to a process to prepare these precursors and their use, especially to give MGMA or MGDA.

16 Claims, 3 Drawing Sheets

(56) References Cited

FOREIGN PATENT DOCUMENTS

| WO | 2014/135403 A1 | 9/2014 |
| WO | 2015/036324 A1 | 3/2015 |

OTHER PUBLICATIONS

International Preliminary Report on Patentability for PCT/EP2015/080837 dated Nov. 18, 2016.
Neal G. Anderson; Practical Process, Research & Development; Jul. 30, 2008; p. 27-p. 53; p. 233-p. 259. (Submitted here in original English Version as well as cited Japanese translation.).

* cited by examiner

CRYSTALS OF ALANINE N-ACETIC ACID PRECURSORS, PROCESS TO PREPARE THEM AND THEIR USE

This application is a national stage filing under 35 U.S.C. § 371 of PCT/EP2015/080837, filed Dec. 21, 2015, which claims priority to European Patent Application No. 14200045.4 filed Dec. 23, 2014, the contents of which are each incorporated herein by reference in their entireties.

The synthesis of aminoacetonitriles has been described in various patents. Several of these nitriles have been commercially available for a long period already. EDTN (ethylene diamine tetraacetonitrile), PDTN, (propylene diamine tetraacetonitrile) and NTAN (nitrilotriacetonitrile) are known examples. These nitriles are available as solids and they are isolated by precipitation from the aqueous nitrile reaction mixture.

U.S. Pat. No. 2,511,487 describes the synthesis of IDAN, iminodiacetonitrile, which is isolated from its reaction mixture. The isolation of methylene bisiminodiacetonitrile has been described using a continuous process in U.S. Pat. Nos. 3,679,729 and 3,679,728. An extensive list of amines used to prepare aminoacetonitriles is given in U.S. Pat. No. 4,478,759; however, in the list of amines given in this document there is no amino acid. Special acetonitriles, containing an unsaturated bond, have been described as being isolated in U.S. Pat. No. 4,510,099. None of the above prior art documents discloses the preparation of an acetonitrile that contains a carboxylate functionality.

For a few decades now, there has been increased interest in a readily biodegradable chelate to replace NTA (nitrilotriacetic acid, a readily biodegradable chelate) that is suspected to be carcinogenic.

Some chelating agents that were found to be readily biodegradable and non-hazardous are chelating agents based on natural amino acids. Such chelating agents inherently contain a carboxylic acid group that is derived from the amino acid part in their structure. MGDA, methylglycine N,N-diacetic acid, is an example of such a biodegradable chelating agent. MGDA can be prepared by several processes. Processes with a nitrile as intermediate are described in U.S. Pat. Nos. 8,802,894, 7,754,911 and US2012/0184769. The intermediate in the processes disclosed in the above documents is MGDN (methylglycine nitrile N,N diacetonitrile) and this acetonitrile is isolated in solid form by crystallization.

U.S. Pat. No. 5,786,313 (Example 2) describes a MGDA preparation process that starts with D,L-alanine as raw material. This process proceeds through the alanine N,N-diacetonitrile intermediates. However, in the document isolation of the acetonitrile is neither disclosed nor suggested. Other examples in this patent result in acetonitriles without any carboxylate functionality, such as the above MGDN. U.S. Pat. No. 5,849,950 provides in Example 1 the recipe to synthesize D,L-alanine diacetonitrile using D,L-alanine. Again, this document has neither any disclosure on the isolation of the obtained acetonitrile, nor is it acknowledged that it is possible to isolate the acetonitrile in solid form. Additionally US2012/248370 discloses alanine N,N-diacetonitrile as an intermediate in MGDA production, but also in this document the compound is not disclosed to be isolated, let alone that a crystalline form is disclosed. Further in this document it seems that L-MGDA is disclosed only. WO96/30335 discloses alanine monoacetonitrile as an intermediate in MGMA production but again not a single word about isolation thereof in solid form. The same can be said for JP s55 122751. WO 2014/135403 allegedly discloses employing alanine N,N-diacetonitrile as a solid in an Example, but recalculating the molar mass it is more likely that this molecule actually was MGDN, methylglycine nitrile N,N-diacetonitrile, i.e. the molecule wherein the alanine is not present as a carboxylic acid but also in the form of a nitrile. Moreover, also this document neither discloses nor suggests the compound to be crystalline.

WO2009/024519 describes the synthesis of GLDN (glutamic acid N,N-diacetonitrile), which is a nitrile having a carboxylate group that can be converted into GLDA (glutamic acid N,N dicarboxylate), another example of a biodegradable chelating agent based on an amino acid. WO 2009/024519 only exemplifies the isolation of glutamic acid N,N diacetic amide in solid and crystalline form. The dinitrile intermediate GLDN is probably too highly soluble and thereby impossible to isolate in solid form.

Though Applicant does not wish to be bound by theory, it is thought that the presence of carboxylate groups contributes to the increased solubility of acetonitriles, especially when the pH of an aqueous acetonitrile solution is such that dissociation of the carboxylate function can take place.

DETAILED DESCRIPTION

Figure 1:
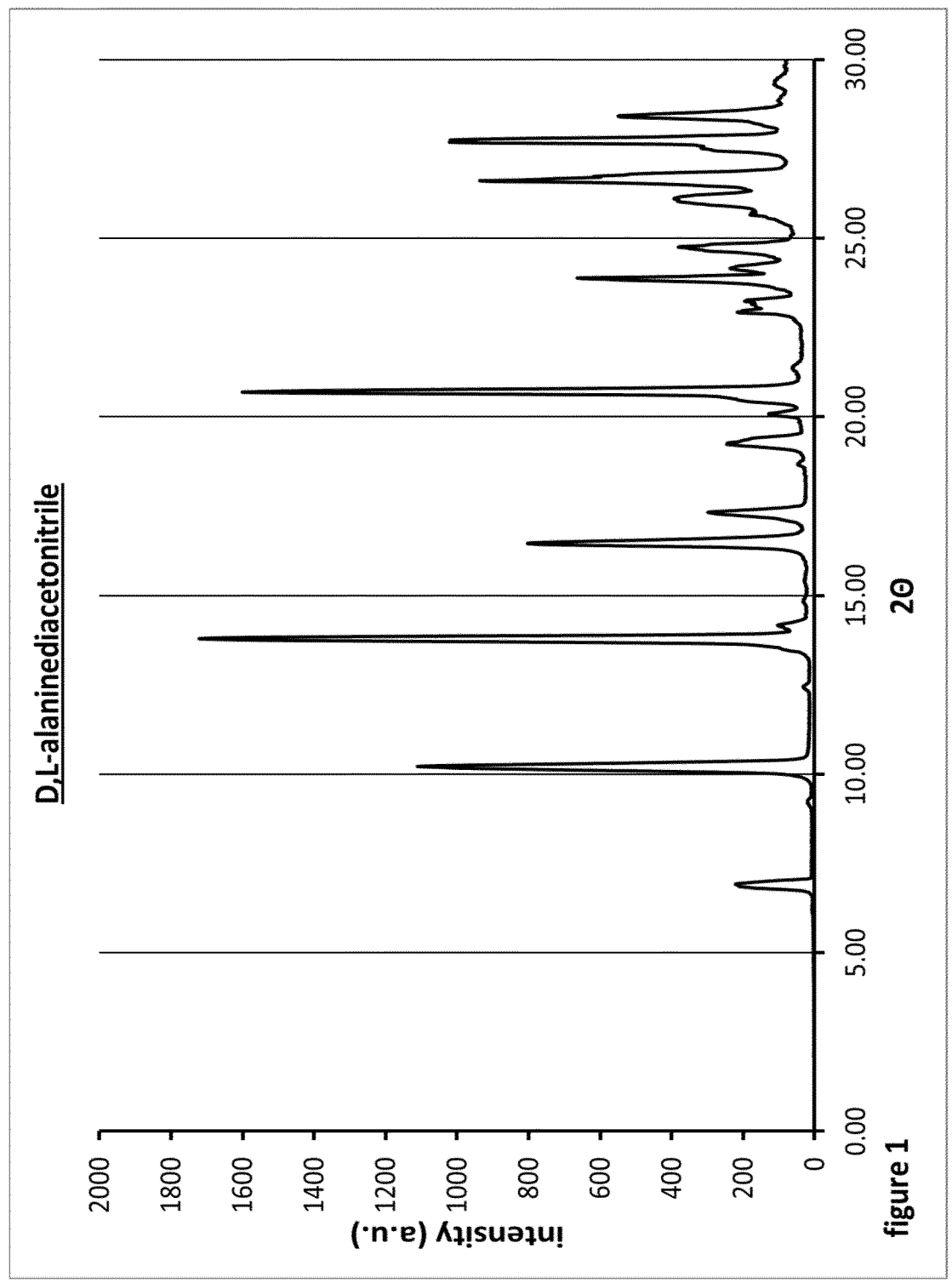
FIG. 1 is a powder diffractogram of D,L-alanine diacetonitrile.

The present invention relates to precursors of alanine N-acetic acid of formula (i) COOM-CH(CH3)—NH—(CH2CN), wherein M is hydrogen (alanine N-monoacetonitrile), or (ii) COOM-CH(CH3)—N—(CH2CN)2, wherein 0 to 50% of all M is sodium or potassium and 50 to 100% of all M atoms is a hydrogen atom (alanine N,N-diacetonitrile and its partial salts) comprising L-alanine to D-alanine in a range of from 75:25 to 50:50 (L:D), or (iii) COOM-CH (CH3)—N—(CH2CONH2)2, wherein M is hydrogen (alanine N,N-diacetamide), and wherein the precursors are in the form of crystals.

The alanine N-acetic acid precursors alanine N-monoacetonitrile and alanine N,N-diacetic amide in a preferred embodiment also comprise L-alanine to D-alanine in a range of from 75:25 to 50:50 (L:D). The compounds containing L-alanine to D-alanine in a range of from 75:25 to 50:50 (L:D) can be said to be partially or fully (when 50:50) racemized.

The invention additionally covers a process to prepare such precursors comprising:
  a first step providing an aqueous solution of the alanine N-acetic acid precursor,
  optionally for the alanine N monoacetonitrile or alanine N,N diacetamide precursor, a second step ensuring the alanine is at least partly racemized, one step after the other in random order or simultaneously, and
  a third step allowing the aqueous solution to crystallize.

The invention finally relates to the use of the above precursors in preparing MGMA or MGDA, as a crystallization inhibitor, in detergents, agriculture, in oil field applications, feedstock applications, pharmaceutical applications, and in water treatment. Hence the present invention also relates to a process of hydrolyzing the precursors of the present invention to give MGMA or MGDA containing a step of preparing an aqueous solution containing the precursors and an alkali metal salt followed by heating such solution.

Any reference in this document to alanine is meant to be a reference to α-alanine, also known as methylglycine.

The alanine N-acetic acid precursors of the present invention include not only precursors in which the amine group of the alanine has been substituted with one acetonitrile group but also alanine N,N-diacetic acid precursors, i.e. precursors wherein the amine group of the alanine has been substituted with two acetonitrile or acetic amide groups.

Contrary to what was thought, it was found to be very well possible to isolate acetonitrile compounds that contain a carboxylate in the form of crystals, to be more specific, N-acetonitrile and N-acetic amide-substituted amino acids were found to be crystalline. Interesting enough, only the acidic version, i.e. the one wherein M in the above formulae is hydrogen, of the alanine N monoacetonitrile precursor can be crystallized and only the acidic version, i.e. again the one wherein M in the above formulae is hydrogen, of the alanine N,N-diacetamide precursor can be crystallized. On the other hand, of the alanine N,N-diacetonitrile precursor also the partial salts, i.e. the compounds of the above formulae wherein up to 50% of all Ms is sodium or potassium, were crystallized, but this diacetonitrile precursor needs to be at least partially racemized before it becomes isolatable in crystalline form.

The alanine N-acetic acid precursors of the present invention can be hydrolyzed to give alanine N-acetic acid or alanine N,N-diacetic acid, also known as methylgycine N-acetic acid (MGMA) or methylglycine N,N-diacetic acid (MGDA), by a process containing the steps of adding together the precursors and an alkali metal salt in an aqueous solution and heating this solution to a temperature of at least 80° C., preferably to boiling point.

In an embodiment of the above hydrolysis process of the precursors to give MGMA or MGDA first a solution of the precursor is prepared, followed by a step wherein the dissolved precursor is added to an aqueous solution of an alkali metal salt with a concentration between 1-50 wt % of the alkali metal salt or more preferably, between 5-25 wt % of the alkali metal salt, at a temperature of 80-98° C. or more preferably, 90-96° C., preferably followed by a step wherein the temperature is raised to boiling temperature. The precursor may also be added as solid to an aqueous solution of an alkali metal salt at a concentration of 1-50 wt % of the alkali metal salt or more preferably, between 5-25 wt % of the alkali metal salt, at a temperature of 105-45° C. or more preferably, at 20-30° C., followed by a step wherein the temperature is raised to at least 80° C., preferably boiling temperature, or by a step wherein the cold hydrolyzed precursors (MGMA/MGDA) are added in the presence of dissolved ammonia to a hot aqueous solution in order to remove ammonia in a controlled way till an ammonia level sufficiently low not to cause an ammonia smell is obtained.

An alternative way of adding together the precursor and the alkali metal salt is dosing of the precursor to water and simultaneously dosing the alkali metal salt solution in such a way that at any moment in time during the reaction a slight excess of free alkali is available. In preferred embodiments the alkali metal salt is chosen from the group of NaOH, KOH, or LiOH, more preferred are NaOH, or KOH.

Isolation of the solid precursors has the advantage of increased storage stability. It prevents the (partial) hydrolysis that will occur for example in aqueous acetonitrile solutions. Long-distance transport will be possible due to increased shelf life and lower costs—no shipment of water. It means that hydrolysis/saponification of the solid precursor can take place independent of the location at which the precursor is synthesized. Because the alanine mono- or dinitrile/alanine diamide precursors can be isolated as crystals and can therefore be stored and transported very well, the precursors can thus be produced in one location and later be further hydrolyzed to methylglycine N-monocarboxylate or methylglycine N,N-dicarboxylate in another location.

Additionally, the increased purity of the precursor solids (compared to the aqueous solution) will provide a less colored and fewer byproducts-containing hydrolyzed product.

According to this invention, a solid compound is crystalline (or a crystal) when it has a three-dimensional periodic structure (crystal). A three-dimensional periodic structure is different from an amorphous structure in that it shows interference in monochromatic X-ray diffraction which fulfills the Bragg equation ($2 d \sin \Theta = n\lambda$), whereas amorphous materials produce a broad background signal. The crystalline particle of the present invention further exhibits reduced hygroscopicity compared to the same in the amorphous form.

The biodegradable crystalline salts of the invention preferably comprise L- to D-alanine in a range between 75:25 and 50:50 (L:D), i.e. it was found that in order to be able to obtain crystals, it is advantageous if the alanine is at least partially racemized and essential if one desires to isolate alanine N,N-diacetontrile as a crystal. The crystals preferably comprise L-alanine:D-alanine between 60:40 and 50:50, even more preferably L-alanine to D-alanine as an (about) 50:50 mixture of equal quantities of the two enantiomers L-alanine and D-alanine, i.e. the product is a racemic mixture of (more or less) equal quantities of the two enantiomers of alanine wherein the (partially) racemized products are also readily biodegradable according to standard OECD tests just as optically pure (L-) product. Each enantiomer rotates the plane of polarization of plane-polarized light through a characteristic angle, but because the rotatory effect of each component exactly cancels that of the other, the 50:50 racemic mixture is optically inactive.

In a preferred embodiment the precursors of the present invention are alanine N,N-diacetonitrile or the partial sodium or potassium salts thereof, as these diacetonitrile group-containing precursors were found the easiest to crystallize.

In a further preferred embodiment the precursors of the present invention are alanine N-monoacetonitrile crystals showing the following main characteristic reflections: $2\Theta = 13.3$; 20.3; 21.4; 21.9; 24; 0 (accuracy of +/−0.1); alanine N,N-diacetonitrile crystals with the following main characteristic reflections: $2\Theta = 6.9$; 10.2; 13.8; 14.1; 16.5; 17.3; 19.3 (accuracy of +/−0.1); or alanine N,N-diacetonitrile sodium salt (0.5 eqv) crystals with the following main characteristic reflections: $2\Theta = 7.1$; 10.8; 14.3; 14.8; 18.2; 20.7; 21.0; 23.3 (accuracy of +/−0.1)

The crystals of the invention in one embodiment have a particle size of 20 to 2,000 microns (μm), preferably of 50 to 1,000 microns.

In one embodiment the alanine N-acetic acid precursor is prepared (as a first step of the process) by what is known as a Singer route. The reaction route encompasses reacting alanine or partially neutralized alanine with 0.8-2.4 molar equivalents of formaldehyde and 0.8-2.4 molar equivalents of hydrogen cyanide, to first give alanine mono- or diacetonitrile (or the monoalkali metal salt thereof). These types of products are known as aminoacetonitriles or, for short, "nitriles". Nitriles can be partially hydrolyzed to give acetic amide or, for short, "amides". The process may optionally be performed in the presence of an alkali metal hydroxide.

In a preferred embodiment the reaction to prepare the alanine N-acetic acid precursor can be performed by reacting alanine or partially neutralized alanine with 0.8-2.4 molar equivalents of formaldehyde and 0.8-2.4 molar equivalents of hydrogen cyanide, wherein the reaction takes place by simultaneous dosing of both the formaldehyde and the hydrogen cyanide, or by dosing at least 40% of the amount of formaldehyde before dosing of the hydrogen cyanide is started. The addition of formaldehyde and hydrogen cyanide preferably takes place at a temperature between 0° C. and 40° C.

In a more preferred embodiment of the process to prepare primarily the disubstituted compounds of the invention, between 1.6 and 2.4 equivalents of formaldehyde are used per equivalent of alanine or salt thereof and 1.6 to 2.4 equivalents of HCN are used per equivalent of alanine or salt thereof. In an even more preferred embodiment 1.9-2.1 equivalents of formaldehyde and HCN are used per equivalent of alanine or salt thereof. Most preferably, the amount of formaldehyde and HCN is about 2.0 equivalents per equivalent of alanine or salt thereof. In the process the amount of HCN may be (but does not need to be) the same as the amount of formaldehyde.

Instead of starting with alanine, it is possible to use sodium or potassium salt thereof or a partially neutralized sodium or potassium salt of alanine (i.e. $Na_y$-alanine or $K_y$-alanine wherein y is more than 0 but less than 1). The same holds for hydrogen cyanide and sodium hydroxide; sodium cyanide, potassium cyanide, and potassium hydroxide are alternatives as long as during the reaction the pH is acidic or neutral or only slightly alkaline and does not become too alkaline (preferably it stays below 10).

In the above process, the low solubility of alanine can be overcome by dissolving it in NaOH or KOH, resulting in the formation of monosodium or monopotassium alanine or a mixture of the acid and the salt (which has been referred to hereinabove as neutralized or partially neutralized alanine).

As the nitriles are relatively stable in acidic conditions, it may be advantageous to add a small amount of a well-known acid, like hydrochloric acid or sulfuric acid, to control the pH.

In the case of the potassium version of the nitrile, the final nitrile concentration can be higher due to the high solubility of potassium alanine. It allows for more economical transport, more output per reactor volume, lower energy costs, and is an easy way to produce a high amount of MGMA or MGDA in the hydrolysis of the nitrile functionalities.

In one embodiment of the process of the invention, a suitable way of ensuring that the alanine is at least partly racemized (as the—optional—second step) is using D,L-alanine as a raw material in the first step of the process.

In a preferred embodiment, the process of the invention before performing the third step includes a concentrating step that is carried out until the solution has a concentration of equal to or more than 15 wt % to up to or equal to 80 wt % of the alanine N acetic acid precursor, based on the weight of the aqueous solution, more preferably more than 20 wt % up to or equal to 80 wt % of precursor, based on the weight of the aqueous solution. When the more concentrated solutions are so viscous that an efficient crystallization becomes more difficult, the skilled person will know that reducing the viscosity thereof, for example by heating the solution, may be desirable.

In a further embodiment, the aqueous solution may be concentrated in the concentrating step by way of evaporation, optionally at an elevated temperature.

It is also preferred that in the solution containing the precursor that is allowed to crystallize in the third step of the process at least 75 wt % of the total organic compounds is precursor. Organic compounds are defined as hydrocarbon based compounds (compounds that contain at least one covalent hydrogen-carbon bond) and include compounds that can be considered impurities formed during the preparation of the alanine N acetic acid precursor (such as formaldehyde, nitrilotriacetic acid, alanine, glycolic acid, formic acid). More preferably, at least 85 wt % on the total weight of organic compounds in the solution is an alanine N acetic acid precursor, most preferably at least 90 wt %.

In yet another preferred embodiment, the weight amount of alanine N acetic acid precursor on total inorganic compounds in the solution, i.e. the weight ratio precursor:inorganic compounds, in the solution allowed to crystallize is higher than 1:1, more preferably higher than 2:1, and most preferably higher than 3:1, wherein inorganic compounds are compounds that are not organic compounds as defined above and not water. Inorganic salts are the most important examples of inorganic compounds.

In another preferred embodiment the third step comprises crystallization by allowing the solution to stand for an extended period of time and/or cooling and/or seeding, and/or comprises spraying the aqueous solution of the second step on seeding crystals, such as is done in a spray granulation process.

When a cooling step is performed in the third step, cooling may be batch controlled-cooling, e.g. using pre-determined temperature profiles.

When seeding is done in the third step to allow the product to crystallize, the seeding may for example comprise adding dust and/or glass particles, crystals of the respective crystalline compound. Seeding may be carried out by way of macro- or micro-seeding, temperature shocks, vibration and/or providing a suitable surface for adhesion. Seeding may be carried out at elevated temperatures and/or stepwise.

Even more preferably in the process of the present invention the third step is performed at a temperature of below 40° C.

In a further embodiment, the process according to this invention may further comprise an optional separation step, wherein the crystalline product of the third step is separated from the mother liquor (that part of the aqueous solution which is left after crystallization).

The process according to this invention may optionally comprise a drying step in which the crystalline particle of the precursor is dried. Drying may be conducted at elevated temperatures and/or under reduced pressure, preferably vacuum.

The process of the invention can be performed as a batch process, semi-continuously or continuously. Preferably, the process is a continuous process. The process according to this invention can be carried out as a continuous process, e.g. by using resulting products as seeds in the third step. Crystallization may also be induced repeatedly in the separated mother liquor.

EXAMPLES

In all Examples where reference is made to diffractograms, these were made using the following procedure: Samples were ground to a powder in a mortar and put in a standard sample holder of a Bruker-AXS D8 reflection-diffractometer. Samples were measured with nickel filtered Cu-Kα radiation and generator settings 40 kV, 35 mA. The slits used were: divergence and anti-scatter slit V20, detector slit 0.2 mm. The measuring range was: 2θ=0.50-80.0°, with a step size of 0.02° and a time per step of 1.4 seconds Example 1

The Synthesis and Crystallization of D,L-Alanine Diacetonitrile

A 3 L reactor was charged with 545 g D,L-alanine and 330 g water. Whilst stirring 851 g formaldehyde-43.8% (2 mole eq) were dosed in 15 minutes at room temperature. After the formaldehyde dosing had been completed, 338 grams HCN were dosed. The reaction was exothermic and cooling needed to be applied; the temperature of the reaction mixture during HCN dosing was controlled and kept at 30° C. When HCN dosing was complete, the mixture was stirred for another hour at 30° C. before it was cooled down.

At circa 20° C. crystallization started and the mixture was kept at 20° C. overnight to facilitate crystal growth and further crystallization. The next day most of the crystals were removed before further cooling of the reaction mixture to zero degrees Celsius. When the mixture had been stirred for several hours at 0° C., it was centrifuged to remove all solids.

The solids after drying, being 850 grams, were analyzed by NMR and mass spectrometry. Microscope pictures and the recorded diffractogram showed that the solids were crystalline. The crystals were identified as highly pure D,L-alanine diacetonitrile. From X-ray diffraction analysis (using Cu Kα radiation) it appeared that the crystalline powder obtained consisted of a mixture of crystalline varieties closely resembling unit cell parameters in the range of:
a=26.3+/−0.1; b=9.2+/−0.05; c=7.4+/−0.05; y=102+/−0.5, and space group C 2/c;
yielding the following list of main characteristic reflections (on using Cu Kα radiation):
2Θ=6.9; 10.2; 13.8; 14.1; 16.5; 17.3; 19.3 (accuracy of +/−0.1)
as demonstrated also in the powder diffractogram given in FIG. 1.

Comparative Example 2

The Synthesis of L-Alanine Diacetonitrile

Exactly the same procedure was followed, but instead of using D,L-alanine the optically pure L-alanine was used.

When the HCN dosing was completed and the reaction mixture was slowly cooled down, no crystallization was observed. The reaction mixture was analyzed by $^1$H and $^{13}$C NMR and consisted of alanine diacetonitrile. This solution was stored at 5° C. for over 2 weeks, but crystallization could not be induced. It proved impossible to isolate L-alanine diacetonitrile crystals using the same procedure as in Example 1.

Example 3

Solubility and Stability of D,L-Alanine Diacetonitrile Crystals

The solubility of D,L-alanine diacetonitrile was determined at various temperatures to get a clear understanding of the solubility and stability of D,L-alanine diacetonitrile. The D,L-alanine diacetonitrile crystals obtained in Example 1 were added to demi-water and the samples in well-closed bottles were placed in ovens/refrigerators at various temperatures overnight. The next day the samples were visually inspected for solids and the aqueous layers were analyzed by NMR for composition to check if the D,L-alanine diacetonitrile had been hydrolyzed; no or very little hydrolysis took place.

TABLE 1

Solubility of D,L-alanine diacetonitrile at various temperatures.

| temp. ° C. | wt % D,L-alanine diacetonitrile |
| --- | --- |
| 0° C. | 6 |
| 5° C. | 7.9 |
| 20° C. | 40.7 |
| 30° C. | 75 |
| 40° C. | 82.5 |
| 50° C. | 95 |

Example 4

The Synthesis and Isolation of Crystalline D,L-Alanine Monoacetonitrile

A 3 L jacketed glass reactor was charged with 545.3 g (5.92 moles) D,L-alanine (Sigma Aldrich) and 327 g water (62.5 wt % aq. alanine sol.). At a temperature of 20° C. whilst stirring ~1 equivalent of formaldehyde 44 wt % (=419.2 g/6.15 moles) was dosed to the slurry in circa 15 minutes. No clear exothermal effect was observed during dosing. 166 grams of HCN (~6.15 moles) were slowly dosed to the slurry. During dosing of the HCN crystallization took place, no clear solution was obtained. The slurry started to solidify very quickly. Additional water was added, 916 grams, and the reaction temperature was increased gradually to 60° C. A clear pale yellow solution was obtained. Solids were formed after cooling down the reaction mixture and the slurry was centrifuged. The 250 grams of wet cake consisted of small crystals The obtained wet cake was crystallized by the following procedures:

Procedure A 110 grams of alanine mononitrile wet cake were charged to 500 g water and the temperature was raised to 75° C., at which the reaction mixture became clear, resulting in a saturated solution. The solution was allowed to cool to room temperature. During cooling crystallization started. The crystals were separated from the mother liquor by centrifuging. The crystals were dried under vacuum at 25° C.

Procedure B 110 grams of alanine mononitrile wet cake were charged to 500 g water and the temperature was raised to 75° C., at which the reaction mixture became clear, resulting in a saturated solution. Circa 500 ml ethanol were added and the batch was seeded with crystals of the previous recrystallization. The reactor content was slowly cooled to 0° C. The slurry was centrifuged and the wet cake was washed with ice water during centrifuging. The fine crystals were dried under vacuum at 25° C.

Figure 2:
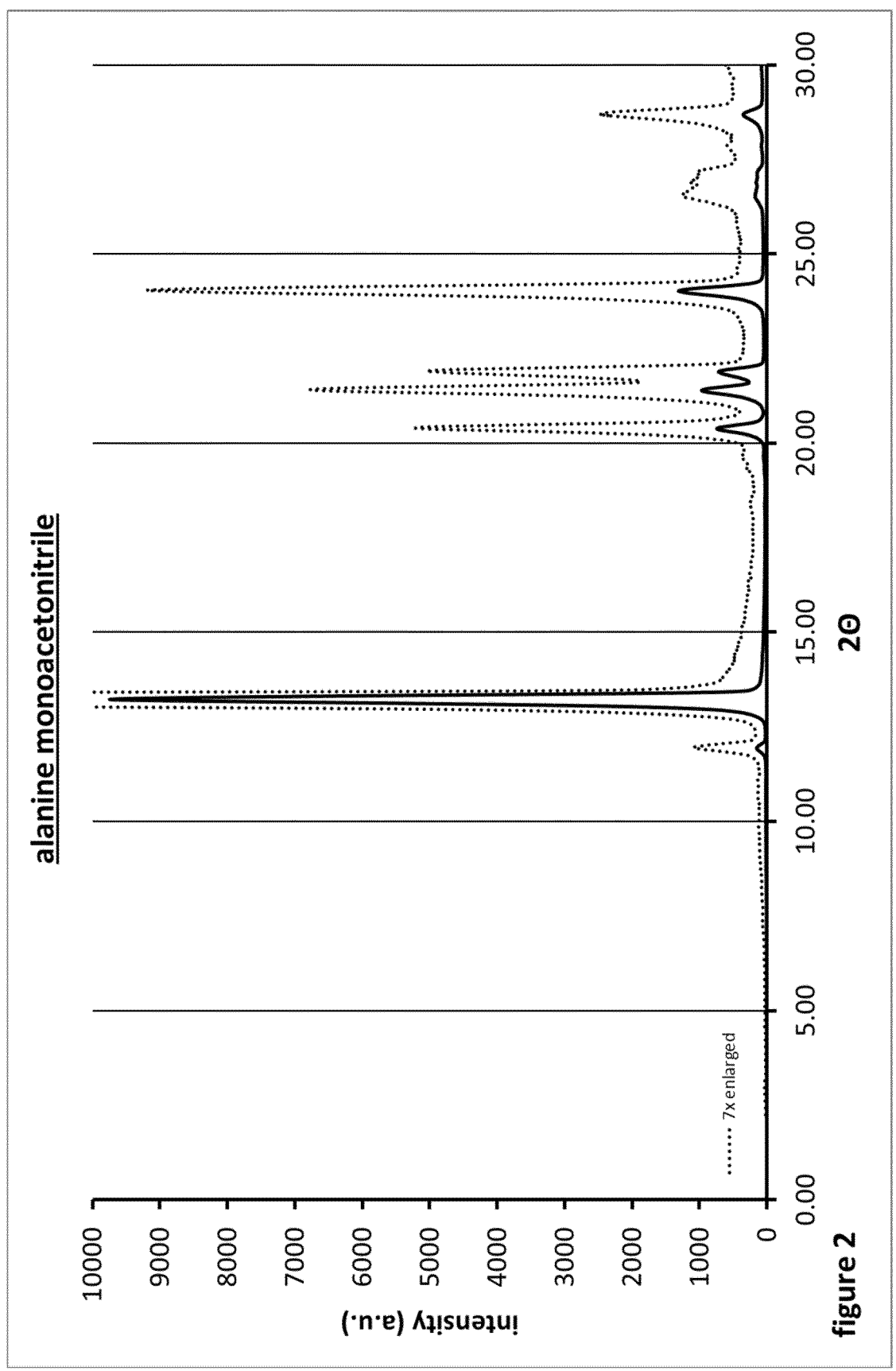
FIG. 2 is a powder diffractogram of alanin monoacetonitrile.

Results of the 600 MHz $^1$H NMR displayed a purity of >99 wt % pure D,L-alanine monoacetonitrile containing only traces of impurities; X-ray diffraction analysis (using Cu Kα radiation) of the crystalline powder yielded the diffractogram of FIG. 2, showing the following main characteristic reflections:

2Θ=13.3; 20.3; 21.4; 21.9; 24.0 (accuracy of +/−0.1)

Further analysis showed that the diffraction pattern could be described using the following unit cell parameters:

a=7.4+/−0.05; b=5.75+/−0.05; c=8.15+/−0.05; β=115.5+/−0.5, and space group P 2₁

Example 5

The Synthesis and Isolation of Crystalline D-Alanine Monoacetonitrile

D-alanine (177.4 grams~2 moles) was pre-charged to a 3 liter glass reactor together with 365 grams of water and stirred. The first equivalent of formaldehyde 44 wt % was dosed at a temperature of 25° C. After that the second equivalent of formaldehyde was dosed simultaneously with both equivalents of HCN in 60 minutes keeping the temperature below 30° C.

During the synthesis of D-alanine diacetonitrile a precipitate was formed (pH reaction mixture 3.3). The precipitate consisted of small particles of unequal size that mainly floated on top of the fluid during the HCN dosing.

A sample was taken of this fluffy precipitate and analyzed by NMR.

Analysis of the precipitate showed that this consisted mainly of D-alanine mononitrile in addition to unconverted D-alanine and D-alanine dinitrile. To further purify the precipitate it was dissolved in water, concentrated at 20 mbar 40° C. and cooled down. The recrystallized D-alanine monoacetonitrile was >92 wt % pure and contained small amounts of D-alanine and D-alanine dinitrile.

Example 6

The Synthesis and Isolation of Crystalline L-Alanine Monoacetonitrile

L-alanine (177.4 grams~2 moles) was pre-charged to a 3 liter glass reactor together with 365 grams of water and stirred. The first equivalent of formaldehyde 44 wt % was dosed at a temperature of 25° C. After that the second equivalent of formaldehyde was dosed simultaneously with both equivalents of HCN in 60 minutes keeping the temperature below 30° C.

During the synthesis of L-alanine diacetonitrile a precipitate was formed (pH reaction mixture 3.3). The precipitate consisted of small particles of unequal size that mainly floated on top of the fluid during the HCN dosing.

A sample was taken of this fluffy precipitate and analyzed by NMR.

Analysis of the precipitate showed that this consisted mainly of L-alanine mononitrile in addition to unconverted L-alanine and L-alanine dinitrile. To further purify the precipitate it was dissolved in water, concentrated at 20 mbar 40° C. and cooled down. The recrystallized L-alanine monoacetonitrile was >92 wt % pure and contained small amounts of L-alanine and L-alanine dinitrile.

Example 7

The Synthesis and Isolation of Crystalline Sodium Salt of D,L-Alanine Diacetonitrile A 1 L reactor was charged with 178.2 g D,L-alanine (1.93 moles) and 120.0 g NaOH-50 (1.5 moles)

The reaction temperature was set to 10° C. Formaldehyde 44 wt % (276 grams/4.05 moles) was dosed at a rate that allowed the temperature of the reaction mixture to be kept below 30° C.

The pH of the reaction mixture became pH=8.4. The yellow solution was slightly viscous. The reactor contents were further cooled to 15° C. and HCN dosing (110 grams/4.07 moles) was started, which was completed in 1 hour. The mixture was stirred for 45 minutes at 30° C., seeded with D,L-alanine diacetonitrile crystals and cooled down to 15° C. Below 25° C. the mixture became turbid due to nucleation. After stirring the reactor content for c. 2 hours the slurry was centrifuged and 102 g of white crystalline wet cake were isolated.

The wet cake was dried and analyzed by NMR, XRD, DSC, TGA, ICP.

Additionally the pH was measured as 1 wt % D,L-alanine diacetonitrile in water and this pH was compared to the pH of 1 wt % D,L-alanine diacetonitrile.

| | |
|---|---|
| pH (1% in water) of D,L-alanine diacetonitrile-Na | pH = 3.3. |
| pH (1% in water) of D,L-alanine diacetonitrile-H | pH = 2.2 |

Figure 3:
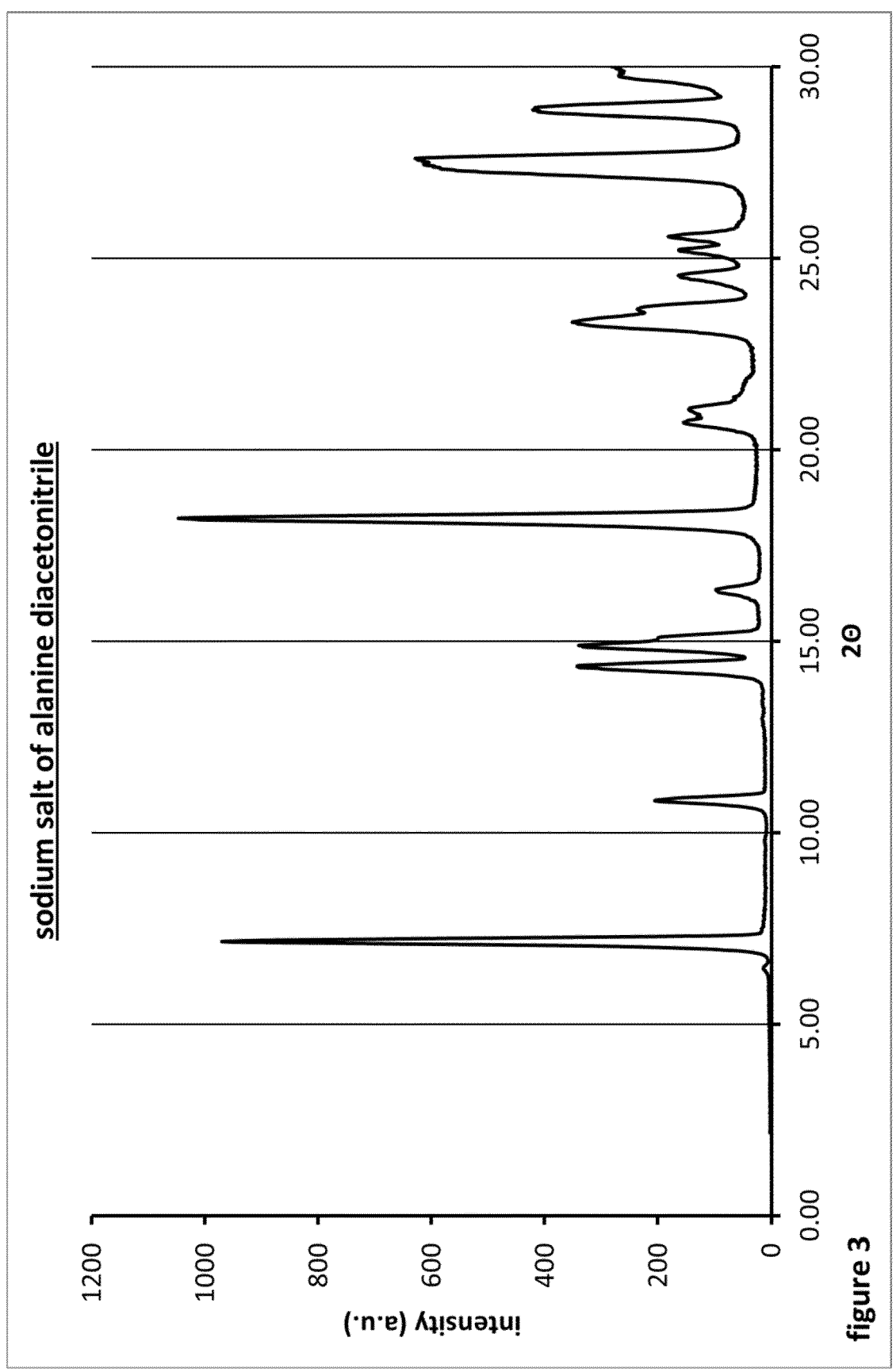
FIG. 3 is a powder diffractogram of sodium salt of D,L-alanine diacetonitrile.

X-ray diffraction analysis of the crystalline powder (using Cu Kα radiation) yielded the diffractogram of FIG. 3, showing the following main characteristic reflections:

2Θ=7.1; 10.8; 14.3; 14.8; 18.2; 20.7; 21.0; 23.3 (accuracy of +/−0.1)

Further analysis showed that the diffraction pattern could be described using the following unit cell parameters:

a=24.75+/−0.1; b=8.65+/−0.05; c=8.45+/−0.05, and space group Pbcn

The isolated crystals were analyzed by inductive coupled plasma on sodium. The wt % sodium in the crystals is ~6.2 wt %, indicating that for each alanine diacetonitrile circa 0.5 equivalent sodium is present, as pure alanine diacetonitrile sodium contains 12.15 wt % sodium. X-ray diffraction analysis of single crystals proved that the unit cell described above contained 8 alanine diacetonitrile units and 4 sodium ions.

Example 8

The Synthesis of Sodium Salt of D,L-Alanine Monoacetonitrile but Crystallization of the Acidic D,L-Alanine Monoacetonitrile A 1 L glass reactor was charged with 64 grams crystalline D,L-alanine monoacetonitrile, 556 grams water and 20.1 grams NaOH (50%). As soon as all solids were dissolved the mixture was concentrated by evaporation of water at 10 mbar and 45° C. until the solution became turbid. The mixture was then allowed to cool to room temperature and the obtained crystals were separated from the fluid with a centrifuge. The solid material was collected and analyzed. Analysis showed that the crystalline material was actually D,L-alanine monoacetonitrile in the acid form.

Example 9

The Synthesis of Sodium Salt of L-Alanine Diacetamide but Crystallization of the Acidic L-Alanine N,N-Diacetic Amide A solution of L-alanine diacetamide sodium salt was prepared by dissolving 50 grams L-alanine diacetamide in 445 grams water and 10.1 grams NaOH (50%) at room temperature. The clear solution concentrated in a Rotavapor at 10 mbar and 45° C. until the solution became turbid again. Then the mixture was allowed to cool to room temperature and the obtained crystals were isolated with a centrifuge. Analysis showed that the obtained crystals were mainly L-alanine diacetamide in the acid form.

Example 10

Synthesis of MGDA by Hydrolysis of Crystalline Alanine Diacetonitrile

A 1 L jacketed stainless steel reactor was precharged with 45 g NaOH-50%+105 g water. The reactor content was heated to 91° C. (Tbath=96° C.). A solution of 175 g alanine diacetonitrile in 408.3 g water (9.72 g/min) and 227.6 g NaOH-50% solution were dosed simultaneously in 60 and 55 minutes, respectively (=9.72 and 4.14 g/min). After dosing, the reaction mixture was heated to boiling temperature. The boiling temperature was controlled by suppletion of water, kept at 110° C. After 2 hours the reaction mixture was cooled to 70° C. and bleaching took place. After stirring for 1 hour the product was cooled to room temperature.

Ultimately 645.5 g of product were retrieved having a sequestering value expressed as Fe-total sequestering value of Fe-TSV=43.1 wt %

Example 11

Synthesis of MGMA by Hydrolysis of Crystalline L-Alanine Monoacetonitrile

A 1 L jacketed stainless steel reactor was pre-charged with c. 570 grams KOH as 10% solution. The temperature of the caustic was kept at 25° C. while c. 128.1 grams (1.0 mole) crystalline L-alanine monoacetonitrile were added portionwise to the caustic solution in 120 minutes at 25° C. After all crystalline L-alanine monoacetonitrile was dissolved the temperature was raised until the solution started to boil. The boiling temperature was controlled by suppletion of water and maintained for c. 2 hours. After cooling to room temperature the final product was collected. The final product consists mainly of the potassium salt of MGMA.

Example 12

Synthesis of D,L-Alanine Diacetonitrile Using NaCN

A 3 liter glass reactor vessel was pre-charged with 178.2 grams D,L-alanine ex Sigma Aldrich (2 moles) and 250 g water to obtain a slurry. Subsequently 278.5 g (2.02 moles) of a 43.5% formaldehyde solution were dosed while keeping the temperature at 20° C. In the second step c. 667.4 g (2.04 moles) of a 30% NaCN solution were dosed simultaneously with 496.6 g HCl 30% (2.04 moles) to the alanine/formaldehyde mixture in 120 minutes while keeping the temperature below 35° C. A post-reaction time of 60 minutes at 25° C. was applied, resulting in a solution (solution A) with a theoretical concentration of 17.8 wt % D,L-alanine diacetonitrile and 12.7 wt % NaCl. From this solution 1,288 g was transferred to a Rotavapor and concentrated to a theoretical concentration of 23.0 wt % D,L-alanine diacetonitrile at 35° C. and vacuum. The clear solution was then cooled to 0° C. and after two hours the obtained precipitate was separated from the solution with a centrifuge. The white crystals were dried in a vacuum oven at 25° C. and analyzed by NMR, inductive coupled plasma and capillary zone electrophoresis. The crystals contained about 4 wt % sodium chloride and the rest was highly pure D,L-alanine diacetonitrile.

FIGURES

Diffractograms of several alanine acetonitriles made using X-ray diffraction analysis (using Cu Kα radiation)

The invention claimed is:

1. An alanine N-acetic acid precursor selected from the group consisting of:
   (a) alanine N-monoacetonitrile of formula COOM-CH(CH3)—NH—(CH2CN), wherein M is hydrogen, said alanine N-monoacetonitrile showing X-ray diffraction reflections at 2θ=13.3; 20.3; 21.4; 21.9; 24.0 with an accuracy of ±0.1,
   (b) alanine N,N-diacetonitrile and its partial sodium salts of formula COOM-CH(CH3)—N—(CH2CN)2, wherein greater than 0 to 50% of all M is sodium and 50 to less than 100% of all M is hydrogen comprising L-alanine N,N-diacetonitrile to D-alanine N,N-diacetonitrile, or their respective partial sodium salts, in a range of from 75:25 to 50:50 (L:D), said alanine N,N-diacetonitrile partial sodium salts showing X-ray diffraction reflections at 2θ=7.1; 10.8; 14.3; 14.8; 18.2; 20.7; 21.0; 23.3 with an accuracy of ±0.1, and
   (c) alanine N,N-diacetamide of formula COOM-CH(CH3)—N—(CH2CONH2)2, wherein M is hydrogen, and wherein the precursors is in the form of crystals that exhibit interference in monochromatic X-ray diffraction which fulfills the Bragg equation $2d \sin \theta = n\lambda$.

2. The alanine N-monoacetonitrile or alanine N,N-diacetamide precursor of claim 1 comprising L-alanine N-monoacetonitrile to D-alanine N-monoacetonitrile, or, L-alanine N,N-diacetamide to D-alanine N,N-diacetamide, respectively, in a range of from 75:25 to 50:50 (L:D).

3. Process to prepare the precursors according to claim 1, comprising:
   a first step providing an aqueous solution of the alanine N-acetic acid precursor;
   optionally for the alanine N monoacetonitrile or alanine N,N diacetamide precursor, a second step ensuring the alanine is at least partly racemized, one step after the other in random order or simultaneously, and
   a third step allowing the aqueous solution to crystallize.

4. Process of claim 3, wherein in the first step the alanine N-acetic acid precursor is made by reacting alanine or partially neutralized alanine with 0.8-2.4 molar equivalents of formaldehyde and 0.8-2.4 molar equivalents of hydrogen cyanide, wherein the reaction takes place by simultaneous dosing of both the formaldehyde and the hydrogen cyanide, or by dosing at least 40% of the amount of formaldehyde before dosing of the hydrogen cyanide is started.

5. Process according to claim 3, wherein the second step includes a concentrating step that is carried out until the solution has a concentration of equal to or more than 15 wt % to up to or equal to 80 wt % of the precursor, based on the weight of the aqueous solution.

6. Process according to claim 3, wherein the third step comprises crystallization by allowing the solution to stand for an extended period of time and/or cooling and/or seeding.

7. Process according to claim 3, wherein the third step comprises crystallization by spraying the aqueous solution of the second step on seeding crystals.

8. Process according to claim 3, wherein the third step is performed at a temperature of below 40° C.

9. Process according to claim 3, wherein the process is a continuous process.

10. Process for preparing methylglycine N-acetic acid (MGMA) or methylglycine N,N-diacetic acid (MGDA) comprising the steps of adding together the precursors of claim 1 and an alkali metal salt in an aqueous solution and heating this solution to a temperature of at least 80° C.

11. The alanine N-acetic acid precursor in crystal form of claim 1 that is alanine N-monoacetonitrile showing X-ray diffraction reflections at $2\theta=13.3; 20.3; 21.4; 21.9; 24.0$ with an accuracy of ±0.1.

12. The alanine N-acetic acid precursor in crystal form of claim 1 that is alanine N,N-diacetonitrile showing X-ray diffraction reflections at $2\theta=6.9; 10.2; 13.8; 14.1; 16.5; 17.3; 19.3$ with an accuracy of ±0.1.

13. The alanine N-acetic acid precursor in crystal form of claim 1 that is alanine N,N-diacetonitrile sodium salt showing X-ray diffraction reflections at $2\theta=7.1; 10.8; 14.3; 14.8; 18.2; 20.7; 21.0; 23.3$ with an accuracy of ±0.1.

14. The alanine N-acetic acid precursor in crystal form of claim 1 that is D,L-alanine diacetonitrile having the X-ray powder diffractogram of FIG. 1.

15. The alanine N-acetic acid precursor in crystal form of claim 1 that is D,L-alanine monoacetonitrile having the X-ray powder diffractogram of FIG. 2.

16. The alanine N-acetic acid precursor in crystal form of claim 1 that is D,L-alanine diacetonitrile sodium salt having the X-ray powder diffractogram of FIG. 3.

* * * * *